United States Patent [19]

Brunt et al.

[11] Patent Number: 4,636,476

[45] Date of Patent: Jan. 13, 1987

[54] PRESERVING AGENT AND METHOD OF USE THEREOF

[75] Inventors: Keith D. Brunt, East Bridgford; Frederick R. Higton, West Bridgford, both of England

[73] Assignee: The Boots Company Plc, England

[21] Appl. No.: 723,013

[22] Filed: Apr. 15, 1985

Related U.S. Application Data

[63] Continuation of Ser. No. 557,718, Dec. 2, 1983, abandoned.

[30] Foreign Application Priority Data

Dec. 14, 1982 [GB] United Kingdom ................ 8235596

[51] Int. Cl.<sup>4</sup> ............................................. G01N 33/04
[52] U.S. Cl. ..................................... 436/23; 436/176; 568/701; 568/713; 426/532; 426/654
[58] Field of Search ......................... 422/37; 424/343; 426/532, 654; 436/176, 23; 568/701, 713

[56] References Cited

U.S. PATENT DOCUMENTS

| | | | |
|---|---|---|---|
| 2,282,799 | 5/1942 | Musher | 426/654 X |
| 3,558,788 | 1/1971 | Clark et al. | 426/532 X |
| 3,637,772 | 1/1972 | Klaui et al. | 426/654 X |
| 4,148,891 | 4/1979 | Smink | 424/121 X |

FOREIGN PATENT DOCUMENTS

| | | | |
|---|---|---|---|
| 2113209 | 8/1972 | Fed. Rep. of Germany | 514/727 |
| 56-86106 | 7/1981 | Japan | 514/675 |
| 1215062 | 12/1970 | United Kingdom | 514/727 |

OTHER PUBLICATIONS

Chem. Abstracts, vol. 93, No. 17, 27-10-1980, p. 206, No. 162713g, Columbus, Ohio, US: and JP -A- 80 73 603 (Green Cross Corp.) 03-06-1980.
Milchwissenschaft, vol. 36, No. 2 (1981), pp. 65-68, J. Thomasow et al.: "Bestimmung des Fett-, Eiweiss- und Milchzuckergehaltes von Milch durch Messung der Infraroabsorption mit dem Gerat Multispec", p. 67, col. 1,2.
WO-A-8 200 056 (Bechman Instruments), Example 1.
US-A-4 258 056 (S. Lentsch), Examples 1-5.
Chem. Abstracts, vol. 96, No 9, Mar. 1, 1982, p. 373, No. 74580t, Columbus, Ohio, US; K. Moore: "The Effect of pH, Temperature and Certain Media Constituents on the Stability and Activity of the Preservative, Bronopol.", & J. Appl. Bacteriol. 1981, 51(3), 483-94.
Croshaw et al., J. Pharm. Pharmacol., vol. 16, 1964, Suppl. pp. 127-130T.
Sykes & Smart, American Perfumer & Cosmetics, vol. 84, 1969, pp. 45-49.
Bronopol Technical Bulletin, Jan. 1977, The Boots Company Ltd.
Bryce & Smart, J. Soc. Cosmetic Chemists, vol. 16, 1965, pp. 187-201.

Primary Examiner—David L. Lacey
Assistant Examiner—Michael S. Gzybowski
Attorney, Agent, or Firm—Jacobs & Jacobs

[57] ABSTRACT

A tablet for use in preserving samples of milk for analysis comprises bronopol (2-bromo-2-nitropropane-1,3-diol) and a water-soluble solid organic carboxylic acid, the amount of the organic acid being within the range 0.002-0.07 milli-equivalents per milligram of bronopol. The presence of the organic acid stabilizes the bronopol, thereby providing a tablet with an adequate shelf life. Suitable organic acids include citric acid, tartaric acid, malic acid, adipic acid, succinic acid and fumaric acid.

11 Claims, No Drawings

PRESERVING AGENT AND METHOD OF USE THEREOF

This application is a continuation of Ser. No. 557,718, filed Dec. 2, 1983 now abandoned.

This invention relates to the preservation of samples of milk.

The routine analysis of milk samples, for example the determination of fat, protein and lactose content, is carried out in many dairies and centralised milk testing stations. It is often not convenient to analyse the samples of milk when they are fresh and various chemical preservatives have been used to preserve samples of milk from microbial, especially bacterial, spoilage until it is convenient to analyse them. A preservation period of up to 10 days, for example up to 7 days and often up to 5 days is generally sufficient.

The preservatives that have been used or proposed for use in the preservation of milk samples are not entirely satisfactory. For example, sodium dichromate has been used but has caused the problem of allergic reactions due to frequent contact with human skin and an alternative to dichromate has been sought.

Bronopol(2-bromo-2-nitropropane-1,3-diol) is known to be a suitable compound for preserving milk samples from microbial, especially bacterial, spoilage. In the preservation of milk samples, it is often convenient to use the preservative in tablet form, so that a standard tablet containing the desired amount of preservative can be added to a standard volume of milk. However, when formulated in a simple tablet form with conventional fillers, binding agents and lubricants, bronopol is not sufficiently stable to give the tablet an adequate shelf life. The present invention concerns a tablet containing bronopol wherein the bronopol is stabilised, thereby providing a tablet with an adequate shelf life.

The present invention provides a tablet for use in the preservation of samples of milk for analysis comprising bronopol and a water-soluble solid carboxylic acid, the amount of the organic acid being within the range 0.002 to 0.07 milli-equivalents per milligram of bronopol.

It will be appreciated that the term "water-soluble" denotes an organic acid that has sufficient solubility in water to enable the tablet to be completely soluble in the desired standard sample of milk. A water-solubility at ambient temperature greater than 0.1% w/v is often sufficient, but a value greater than 1% w/v is preferred. Suitable organic acids include, for example, citric acid, tartaric acid, malic acid, adipic acid, succinic acid and fumaric acid. Preferred acids are citric acid, tartaric acid, malic acid and succinic acid. Citric acid is especially preferred.

The amount of organic acid used in the tablet of the present invention is preferably within the range 0.002 to 0.035, especially 0.004 to 0.030 and more especially 0.005 to 0.030 milli-equivalents per milligram of bronopol present in the tablet. Good results are achieved with an amount of organic acid of 0.005–0.011 milli-equivalents per milligram of bronopol present in the tablet.

In general, tablets of the present invention may be suitably designed to give, when added to a standard sample of milk, a concentration of 0.005–0.1% w/v, preferably 0.01A–0.05% w/v and especially 0.02–0.04% w/v of bronopol. The concentration of organic acid in the milk sample must of course not be sufficient to cause the milk to curdle. This concentration of acid depends to some extent on the particular acid used, but we have found that a concentration not greater than 1 milli-equivalent per 100 ml. of milk is usually satisfactory. In general, we prefer to design the tablet to give an organic acid concentration in the milk sample not greater than 0.5 milli-equivalents per 100 ml. of milk, for example not greater than 0.43 milli-equivalents and especially not greater than 0.16 milli-equivalent per 100 ml. of milk. For reasons of tabletting convenience and size, the tablets of the present invention preferably contain 5–30 mg. bronopol.

The tablet of the present invention may be prepared by conventional tabletting methods using an appropriate filler, for example sodium chloride; binding agent, for example polyvinylpyrrolidone, gum acacia or gum tragacanth; and lubricant, for example sodium benzoate. It will be appreciated by those skilled in the art that these tablet excipients must be such that the final tablet is completely soluble in the desired standard sample of milk and that the excipients do not interfere to an unacceptable extent with the methods used in the analysis of the samples of milk. Such methods of analysis are often instrumental methods based on spectroscopy, for example infra-red spectroscopy. For this reason, when milk samples are to be analysed by methods based on infra-red spectroscopy, the tablets of the present invention preferably contain 0.005–0.011 milli-equivalents of organic acid per milligram of bronopol.

One embodiment of the present invention is a method of preserving a sample of milk from microbial spoilage which comprises dissolving a tablet containing bronopol and a water-soluble solid carboxylic acid in a standard sample of milk so as to provide, per 100 ml of milk, 5–100 mg of bronopol and up to 1.0 milli-equivalents of the carboxylic acid. According to another embodiment of the present invention there is provided, per 100 ml of milk, 10–50 mg of bronopol and up to 0.5 milli-equivalents of the carboxylic acid. According to a further embodiment of the present invention there is provided, per 100 ml of milk, 20–40 mg of bronopol and up to 0.16 milli-equivalents of the carboxylic acid.

The following non-limitative example illustrates the invention.

EXAMPLE 1

Tablets were prepared from the following ingredients:

|  | weight in grams |
| --- | --- |
| Bronopol | 2400 |
| Carmoisine (colouring agent) | 60 |
| Plasdone (polyvinylpyrrolidone) | 135 |
| Sodium chloride | 25305 |
| Citric acid monohydrate | 1200 |
| Sodium benzoate | 900 |

The bronopol and sodium benzoate were mixed and milled in a micro-mill. This mixture was thoroughly blended with the sodium chloride, citric acid monohydrate and the carmoisine. The resulting mixture was granulated with a solution of the polyvinylpyrrolidone in industrial methylated spirit. The granules were dried to a water content of 0.5–1.0% (as determined by loss on drying) and then sieved through a 16 mesh B.S.S. sieve. The resulting granules were compressed on a rotary tabletting press to give tablets of weight 150 mg.

These tablets were satisfactorily stable for 18 months after storage at temperatures of 15° C., 30° C. and 40° C.

Similar tablets not containing the citric acid were found to be unstable after storage of 3 months at these temperatures, due to degradation of the bronopol.

EXAMPLE 2

Tablets are prepared as described in Example 1, except that the citric acid monohydrate (1200 g.) is replaced by anhydrous citric acid (1200 g.)

EXAMPLE 3

In a similar way to that described in Example 1, tablets containing 15 mg. bronopol and various organic acids in various amounts were prepared. The tablets had the following compositions:

| ingredient | weight (mg.) |
|---|---|
| Bronopol | 15.0 |
| Carmoisine (colouring agent) | 0.3 |
| Plasdone (polyvinylpyrrolidone) | 0.7 |
| Sodium chloride | 122.0 |
| Sodium benzoate | 6.0 |
| Organic Acid | x |

Tablets were prepared using the following acids:

| Tablets | Acid | x (mg.) |
|---|---|---|
| (A) | tartaric | 4.5 |
| (B) | tartaric | 31.5 |
| (C) | adipic | 6.8 |
| (D) | succinic | 5.5 |
| (E) | malic | 6.27 |
| (F) | fumaric | 5.4 |
| (G) | citric, monohydrate | 0.84 |
| (H) | citric, monohydrate | 4.2 |

The above tablets (A) to (H) were found to be stable after storage at 40° C. for 6 months. Tablets of the same formulation but not containing any organic acid were found to be unstable after storage under the same conditions for 6 months, as shown by degradation of the bronopol.

We claim:

1. A tablet for use in the preservation of milk samples for analysis comprising bronopol and a water-soluble solid carboxylic acid, the amount of the carboxylic acid being within the range of 0.002 to 0.035 milli-equivalents per milligram of bronopol.

2. A tablet according to claim 1 wherein the amount of the carboxylic acid is within the range of 0.005 to 0.030 milli-equivalents per milligram of bronopol.

3. A tablet according to claim 2 wherein the carboxylic acid is citric acid, tartaric acid, malic acid, adipic acid, succinic acid or fumaric acid.

4. A tablet according to claim 2 wherein the amount of the carboxylic acid is within the range of 0.005 to 0.011 milli-equivalents per milligram of bronopol.

5. A tablet according to claim 4 wherein the carboxylic acid is citric acid, tartaric acid, malic acid, adipic acid, succinic acid or fumaric acid.

6. A tablet according to claim 5 wherein the carboxylic acid is citric acid.

7. A method of preserving a sample of milk from microbial spoilage for analysis which comprises dissolving a tablet containing bronopol and a water-soluble solid carboxylic acid in a standard sample of milk so as to provide, per 100 ml of milk, 5–100 mg bronopol and up to 1.0 milli-equivalents of the carboxylic acid.

8. A method according to claim 8 wherein there is provided, per 100 ml of milk, 10–50 mg bronopol and up to 0.5 milli-equivalents of the carboxylic acid.

9. A method according to claim 8 wherein there is provided, per 100 ml of milk, 20–40 mg bronopol and up to 0.16 milli-equivalents of the carboxylic acid.

10. A tablet for use in the preservation of milk samples for analysis comprising bronopol, sodium chloride and a water-soluble solid carboxylic acid, the amount of the carboxylc acid being within the range of 0.002 to 0.07 milli-equivalents per milligram of bronopol.

11. A tablet according to claim 10 wherein the amount of the carboxylic acid is within the range of 0.005 to 0.011 milli-equivalents per milligram of bronopol.

* * * * *